United States Patent
Egger et al.

(10) Patent No.: US 6,425,879 B1
(45) Date of Patent: *Jul. 30, 2002

(54) NEEDLE-LESS INJECTOR

(75) Inventors: Willi Egger, Sambeek; Nicolaas Visser, Boxmeer; Antonie Hendrikus Meijering, Reuver, all of (NL)

(73) Assignee: Akzo Nobel N.V., Arnhem (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/269,382

(22) PCT Filed: Sep. 23, 1997

(86) PCT No.: PCT/EP97/05276

§ 371 (c)(1),
(2), (4) Date: May 10, 1999

(87) PCT Pub. No.: WO98/13085

PCT Pub. Date: Apr. 2, 1998

(30) Foreign Application Priority Data

Sep. 26, 1996 (EP) .............................................. 96202698

(51) Int. Cl.⁷ ................................................. A61M 5/30
(52) U.S. Cl. ........................................... 604/68; 604/67
(58) Field of Search ..................... 604/68–71, 130–131, 604/134–135, 137, 140, 141, 146–147, 181, 182, 183, 187, 218, 223–224, 235, 65, 67

(56) References Cited

U.S. PATENT DOCUMENTS 3,859,996 A * 1/1975 Miizzy et al.
5,480,381 A * 1/1996 Weston

FOREIGN PATENT DOCUMENTS

WO  WO 93 23110 A  11/1993
WO  WO 96 24398 A  8/1996

* cited by examiner

Primary Examiner—Brian L. Casler
Assistant Examiner—LoAn H. Thanh
(74) Attorney, Agent, or Firm—William P. Ramey, III

(57) ABSTRACT

The present invention relates to a needle-less injector having a housing comprising: a chamber defined within said injector for containing liquid to be injected; a liquid outlet for said chamber positioned at the front end of the injector; a dispensing member in contact with the liquid in said chamber and movable in a first direction to reduce the volume of said chamber to cause the liquid contained therein to be expelled through said liquid outlet; an impacting member arranged to strike said dispensing member to cause movement thereof in said first direction; drive means connected to the impacting member for actuating said injector, or permitting actuation thereof, in response to the application of a selected amount of axial pressure, characterized in that the housing is essentially unitary and the chamber, the liquid outlet and the drive means are immobile with respect to the housing, and that the injector comprises a pressure sensor in order to sense the axial pressure, which pressure sensor is connected to switching means to switching means within the housing which are connected to the drive means and a power source for said drive means, and which switching means is capable of establishing contact between the drive means for actuating said injector and the power source when the pressure sensor is actuated by the selected amount of axial pressure.

6 Claims, 1 Drawing Sheet

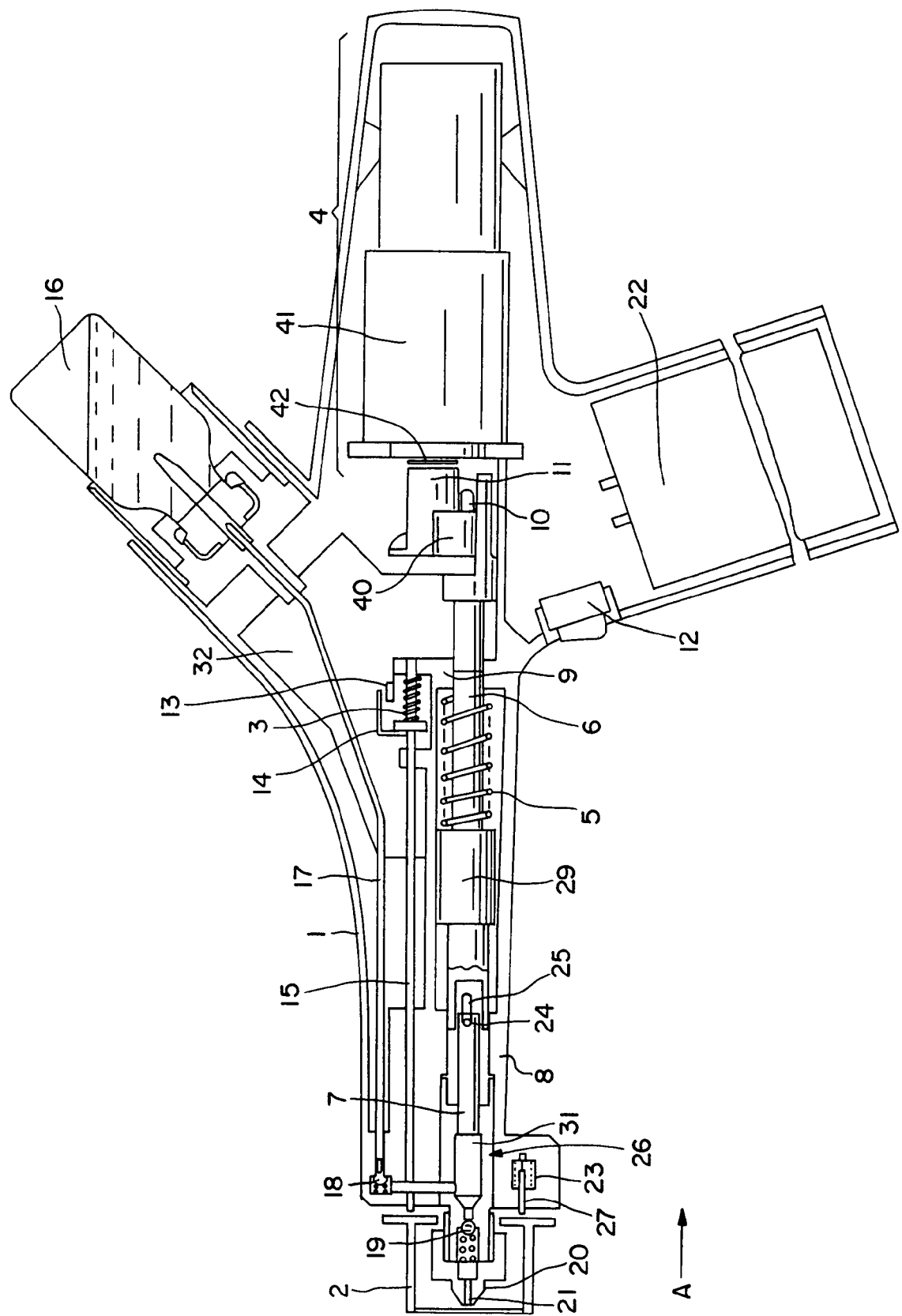

NEEDLE-LESS INJECTOR

BACKGROUND OF THE INVENTION

The invention relates to a needle-less injector having a housing comprising a chamber defined within said injector for containing liquid to be injected; a liquid outlet for said chamber positioned at the front end of the injector; a dispensing member in contact with the liquid in said chamber and movable in a first direction to reduce the volume of said chamber to cause the liquid contained therein to be expelled through said liquid outlet; an impacting member arranged to strike said dispensing member to cause movement thereof in said first direction; and drive means connected to the impacting member for actuating said injector, or permitting actuation thereof, in response to the application of a selected amount of axial pressure.

Such a needle-less injector is known from U.S. Pat. No. 5,480,381. This known needle-less injector has a liquid metering chamber with an outlet orifice, a piston slidable within the metering chamber, and a rod arranged to strike one end of the piston to force liquid through the outlet orifice. A cam follower is mounted at one end of the rod to ride on a cam that retracts the rod away from the piston. The injector is in two parts which are biassed away from each other. Actuation occurs when the two parts of the injector are sufficiently urged towards each other by the user to actuate the drive means in order to move the cam for release of the rod and thereby strike the piston and force liquid through the outlet orifice.

There are several problems attaching to this known injector. One problem is that of lacking accuracy regarding the placement of the cam follower on the highest position of the cam, which is the position of the cam follower when the injector is not used. Due to this construction unintended firing of the injector can occur, for instance due to shocks to which the injector is exposed. This construction gives also rise to occasional repeated firing of the injector when the apparatus is placed on the epidermis of the subject or object to be injected.

When the user urges the two parts of the injector towards each other, actuation occurs by moving a resilient strip to activate a micro switch. The problem associated with this device is that repeated actuation changes the characteristics of this resilient strip, causing a need for readjustment of the injector after a prolonged period of use. A further problem is that the known injector requires careful adjustment after assembly, which is hard and therefore relatively costly. Still another problem is that the accuracy of the amount of liquid be expelled from the chamber containing said liquid, is rather poor and very largely depending on the amount of counterpressure caused by the epidermis of the human, animal or plant on which the injector is placed.

The invention aims to reduce or set aside said problems and the needle-less injector according to the invention is therefore characterized in that the housing is essentially unitary and the chamber, the liquid outlet and the drive means are immobile with respect to the housing, and further that the injector comprises a pressure sensor in order to sense the axial pressure, which pressure sensor is connected to switching means within the housing which are connected to the drive means and a power source for said drive means, and which switching means is capable to establish contact between the drive means for actuating said injector and the power source when the pressure sensor is actuated by the selected amount of axial pressure.

By this construction, the complex two part housing with spring activated movable elements located in said housing as proposed in the state of the art is avoided. The construction according to the invention is simpler, easier to manufacture and to assemble, less costly and safer and more accurate in use.

Consistent with the prior art, the needle-less injector according to the invention has drive means which are connected to the impacting member via a cam and a cam follower for holding the said impacting member away from the said dispensing member against a biasing force, and for releasing the said impacting member to permit it to travel towards and impact against the said dispensing member. According to the invention. however, a preferred embodiment is characterized in that in the unloaded state of the pressure sensor, the cam follower is located near the beginning of the ramp provided by the cam, corresponding with a minimum volume of said chamber for containing the liquid to be injected. This provides more safety to the injector and immunity against shocks which would otherwise lead to premature firing of the injector. This also prevents the above-mentioned occasional repeated firing when the injector is placed on the epidermis of a human, animal or plant.

In a further preferred embodiment, the injector according to the invention is characterized in that in the loaded position of the pressure sensor, the switching means are enabled to establish contact between the power source and the drive means for actuating the injector so as to rotate the cam in order to have the cam follower travel from the beginning of the cam's ramp to the cam's highest position and beyond until it returns to the position near the beginning of the cam's ramp, and correspondingly to effect moving the said impacting member away from the said dispensing member against the biasing force in order to increase the volume of said chamber for containing the liquid to be injected, and, when the cam follower travels beyond the cam's highest position, to effect releasing the said impacting member to permit it to travel towards and impact against the said dispensing member to cause the liquid to be expelled from the chamber through the said liquid outlet, and that the switching means disable further contact between the power source and the drive means until at least the pressure sensor is brought in the unloaded state, and the cam follower has returned to the beginning of the cam's ramp. This avoids the accuracy problems of the injector according to the state of the art which required an accurate positioning of the cam follower on the highest point of the cam just prior to firing when placed against the epidermis of the object to be injected.

In an alternative advantageous embodiment, the injector is provided with a trigger switch, which in its actuated state enables the switching means to establish contact between the power source and the drive means for actuating the injector so as to rotate the cam in order to have the cam follower travel from the beginning of the cam's ramp to the cam's highest position, and remain there by disabling the contact between the power source and the drive means, and correspondingly to effect moving the said impacting member away from the said dispensing member against the biasing force in order to increase the volume of said chamber for containing the liquid to be injected, and that said contact between the power source and the drive means is resumed and maintained, and consequently further rotation of the cam so as to cause the cam follower to travel beyond the cam's highest position is effectuated by simultaneous actuation of the trigger switch and the pressure sensor, until the cam follower returns to the position near the beginning of the cam's ramp so as to effect releasing the said impacting member to permit it to travel towards and impact against the said dispensing member to cause the liquid to be expelled from the chamber through the said liquid outlet, and that the switching means disable further contact between the power source and the drive means until at least the pressure sensor is brought in the unloaded state, and the cam follower has returned to the beginning of the cam's ramp.

The pressure sensor can be electronic or a simple mechanical solution such as a rod extending from the housing; a reliable and preferred mechanical solution is however characterized in that the pressure sensor is a front portion which is movable with respect to the housing by the selected amount of axial pressure from an unloaded to a loaded position.

In a further preferred embodiment, the switching means includes an optical switch, part of which is attached to the front portion so as to establish whether the front portion is in the loaded or the unloaded position.

BRIEF DESCRIPTION OF THE DRAWING

FIG. 1 is a sectional view of the injector according to the invention.

DESCRIPTION OF THE PREFERRED EMBODIMENT

The invention shall now be further elucidated with reference to the drawings of a non-limiting preferred embodiment of the injector according to the invention.

In the drawings a single figure is shown of a sectional view of the injector according to the invention with the components of the injector positioned in a semi-loaded position. The injector comprises a single housing denoted with reference numeral 1, to which a movable front portion 2, sometimes referred to as a pressure sensor, is attached which can be moved in the direction of arrow A when loaded due to placement against the epidermis of a human, animal or plant. A spring 3 via rod 15, and a spring 23 via pin 27 urge the front portion 2 to assume the unloaded position distant from the unitary housing 1. This position is shown in the drawing. The font end of section 1 supports a cylinder 26 with a chamber 31 for the liquid, in which cylinder a piston 7 is sealingly located. The piston 7 is preferably hollow, but closed at both ends, in the case of the righthand end by a hard cap. The cylinder 26 is connected via a non-return valve 18, biassed to its closed position by a compression spring 5, and a tube 17 to a reservoir 16 containing a liquid to be injected. The reservoir has an air inlet (not shown) to permit air to enter the bottle as the liquid is dispensed therefrom. A discharge nozzle 20 is sealingly connected to the chamber 31 within the cylinder 26, and a non-return valve 19, biassed to its closed position by a compression spring, prevents air being drawn into the cylinder during the induction stroke.

The piston 7, sometimes referred to as a dispensing member, is loosely located within a hole in the end of a connecting rod 6, so that it may move freely in a longitudinal direction. A pin 24 is fixed to the piston 7, the pin extending radially therefrom on opposite sides thereof. The pin slides in a slot 25 in the connecting rod 6. The connecting rod 6 is slidingly located in bearings 8 and 9, and urged in the forward direction by a compression spring 5.

A motor-gearbox assembly 41 is housed in the rear end of the housing 1 and the output shaft 42 carries a cylindrical cam 11 to which is engaged a follower 10 attached to the connecting rod 6. The motor is described below as being electric, but could be of some other type, for example gas powered.

In the semi-loaded position shown in the drawing the cam follower 10 is located near the end of a ramp 40 provided by the cam, and the volume of the chamber 31 is near If its maximum due to the fact that in this position the impacting member or piston 7 largely is removed from the area of this chamber 31. In an alternative embodiment having the front portion in the unloaded position, the piston 7 would largely fill the area of this chamber 31, and the cam follower 10 would then be located at the beginning of the ramp provided by the cam 11, When in this latter embodiment of the injector 1 according to the invention the front portion 2 is then moved in the direction of arrow A, an optical switch 13 is activated due to the circumstance that by means of a rod 15, a reflecting member 14 travels inside the housing to activate the optical switch 13. This puts switching means 32, for instance a logic circuit or a small microprocessor, into an enabled state to establish contact between a power source 22 and the drive means 4 due to which the cam 11 will rotate and the cam follower 10 will travel without interruption from the beginning of the ramp provided by the cam 11, up to the highest position thereof and beyond, until it returns back to the position near the beginning of the cam's ramp. The operation of the injector further requires activating a switch 12 providing an enabling input for the above-mentioned switching means 32. In a second alternative embodiment, the switching means 32 could be enabled solely by the switch 12 so as to establish contact between the power source 22 and the drive means 4 so as to cause the cam 11 to rotate, and have the cam follower 10 to travel from the beginning of the cam's ramp up to its highest position, but then remain there in the semi-loaded position as is shown in the drawing until also the front portion 2 is moved from the unloaded into its loaded position. In this latter situation, the cam follower will travel beyond the cam's highest point only if simultaneous actuation of the switch 12 and the front portion 2 occurs, and will continue until the cam follower 10 returns to the beginning of the cam's ramp.

The above-mentioned actuation of the drive means effects moving of the rod or impacting member 6 away from the piston or dispensing member 7 against the biasing force provided by the spring 5. As the connecting rod retracts, the piston 7 initially remains stationary, until the lefthand ends of the slots 25 in connecting rod 6 are contacted by the pins 24 in piston 7. The piston then travels with the connecting rod 6 and draws injection liquid from reservoir 16 into a metering chamber 31 defined in the cylinder 26 between the valve 19 and the lefthand end of the piston 7. At the moment the cam follower 10 travels beyond the cam's highest position, this effects releasing of the rod or impacting member 6 to permit it to travel towards and impact against the piston 7 to cause the liquid which has been drawn into the chamber 31 to be expelled therefrom through liquid outlet 21. After release of the liquid from the metering chamber 31 through liquid outlet 21, the switching means 32 disable further contact between the power source 22 and the drive means 4 until at least the front portion 2 has assumed the unloaded position again as shown in the drawing, and the cam follower 10 has returned to its initial position near the beginning of the cam's ramp.

What is claimed is:

1. A needle-less injector having a housing comprising:
   a chamber defined within said injector for containing liquid to be injected;
   a liquid outlet for said chamber positioned at the front end of the injector;
   a dispensing member in contact with the liquid in said chamber and movable in a first direction to reduce the volume of said chamber to cause the liquid contained therein to be expelled through said outlet;

an impacting member arranged to strike said dispensing member to cause movement thereof in said first direction;

a drive member connected to the impacting member for actuating said injector, or permitting the actuation thereof, in response to the application of a selected amount of axial pressure, wherein the housing is essentially unitary and the chamber, the liquid outlet and the drive member are immobile with respect to the housing, and the injector comprises a pressure sensor in order to sense the axial pressure, which pressure sensor is connected to a switch within the housing which is connected to the drive member and a power source for said drive member and which switch is capable of establishing contact between the drive member for actuating said injector and the power source when the pressure sensor is actuated by the selected amount of axial pressure without requiring the liquid outlet to contact the epidermis of an object to be injected.

2. A needle-less injector according to claim 1, whereby the drive member is connected to said impacting member via a cam and a cam follower for holding said impacting member away from said dispensing member against a biasing force, and for releasing said impacting member or permit it to travel towards and impact against said dispensing member, wherein in an unloaded state of the pressure sensor, the cam follower is located near the beginning of the ramp provided by the cam corresponding with a minimum volume of said chamber for containing the liquid to be injected.

3. A needle-less injector according to claim 2, wherein in an loaded state of the pressure sensor the switch is enabled to establish contact between the power source and the drive member for actuating the injector so as to rotate the cam in order to have the cam follower travel from the beginning of the cam's ramp to the cam's highest position and beyond until it returns to the position near the beginning of the cam's ramp, and correspondingly to effect moving said impacting member away from said dispensing member against the biasing force in order to increase the volume of said chamber for containing the liquid to be injected, and, when the cam follower travels beyond the cam's highest position, to effect releasing said impacting member to permit it to travel towards and impact against said dispensing member to cause the liquid to be expelled from the chamber through said liquid outlet, and that the switch disables further contact between the power source and the drive member until at least the pressure sensor is brought in an unloaded state, and the cam follower has returned to the beginning of the cam's ramp.

4. A needle-less injector according to claim 2 including a trigger switch, wherein in an actuated state of the trigger switch the switch is enabled to establish contact between the power source and the drive member for actuating the injector so as to rotate the cam in order to have the cam follower travel from the beginning of the cam's ramp to the cam's highest position, and remain there by disabling the contact between the power source and the drive means, and correspondingly to effect moving said impacting member away from the said dispensing member against the biasing force in order to increase the volume of said chamber for containing the liquid to be injected, and that said contact between the power source and the drive member is resumed and maintained, and consequently further rotation of the cam so as to cause the cam follower to travel beyond the cam's highest position is effectuated by simultaneous actuation of the trigger switch and the pressure sensor, until the cam follower returns to the position near the beginning of the cam's ramp so as to effect releasing said impacting member to permit it to travel towards and impact against said dispensing member to cause the liquid to be expelled from the chamber through said liquid outlet, and that the switch disables further contact between the power source and the drive member until at least the pressure sensor is brought in the unloaded state, and the cam follower has returned to the beginning of the cam's ramp.

5. A needle-less injector according to claim 1, wherein the pressure sensor is a front portion which is movable with respect to the housing by the selected amount of axial pressure from an unloaded to a loaded position.

6. A needle-less injector according to claim 5, wherein the switch includes an optical switch, part of which is attached to the front position so as to establish whether the front portion is in the loaded or unloaded position.

* * * * *